(12) United States Patent
Shang

(10) Patent No.: US 9,387,007 B2
(45) Date of Patent: Jul. 12, 2016

(54) GLANS RETAINER

(76) Inventor: Jianzhong Shang, Wuhu (CN)

( * ) Notice: Subject to any disclaimer, the term of this patent is extended or adjusted under 35 U.S.C. 154(b) by 407 days.

(21) Appl. No.: 13/522,380

(22) Filed: Jul. 16, 2012

(65) Prior Publication Data

US 2013/0041384 A1     Feb. 14, 2013

Related U.S. Application Data

(63) Continuation of application No. PCT/CN2010/001838, filed on Nov. 16, 2010.

(30) Foreign Application Priority Data

Jan. 28, 2010 (CN) .................. 2010 2 0103272 U

(51) Int. Cl.
*A61B 17/326*     (2006.01)
(52) U.S. Cl.
CPC ................... *A61B 17/326* (2013.01)
(58) Field of Classification Search
CPC ............. A61B 17/326; A61B 17/3209
USPC ............. 606/118, 151, 153, 154, 157
See application file for complete search history.

(56) References Cited

U.S. PATENT DOCUMENTS

| | | | | |
|---|---|---|---|---|
| 2,561,176 A | * | 7/1951 | Buckingham | A61B 17/326 606/118 |
| 5,797,921 A | * | 8/1998 | Cimini | A61B 17/326 606/118 |
| 2004/0215210 A1 | * | 10/2004 | Duel | 606/118 |
| 2012/0203242 A1 | * | 8/2012 | Fuerst | A61B 17/326 606/118 |

FOREIGN PATENT DOCUMENTS

CN    2592136    * 12/2003 ............... A61F 5/00

OTHER PUBLICATIONS

Machine translation of CN2592136.*

* cited by examiner

*Primary Examiner* — Thomas McEvoy
(74) *Attorney, Agent, or Firm* — Thibault Patent Group

(57) ABSTRACT

A glans retainer comprises an annular cover for covering a glans during circumcision surgery. The annular cover may comprise a circular or oval cross section, and is sized to generally match the glans. Fixing straps are connected on the periphery of the annular cover for fixing the annular cover to a circumcision apparatus. Each fixing strap comprises an adhesive layer on its bottom. In one embodiment, six fixing straps are used. When the annular cover is placed over the glans and the fixing straps are connected to the circumcision apparatus, the glans is generally restrained from movement relative to the circumcision apparatus by virtue of the tension in the fixing straps as they hold the annular cover to the glans. Therefore, during removal of the necrotic prepuce, pain is reduced and the probability of bleeding is lowered, making the surgical procedure more safe and reliable.

13 Claims, 1 Drawing Sheet

GLANS RETAINER

CLAIM OF PRIORITY

This application is a continuation of International Application No. PCT/CN2010/001838, having an international filing date of Nov. 16, 2010, which claims owned by the inventor of the present invention, the entire contents of which are incorporated by reference herein.

FIELD OF THE INVENTION

The invention relates to a type of medical device, specifically a glans retainer used in conjunction with a circumcision apparatus.

BACKGROUND

Redundant prepuce or phimosis is one of the causes of male urinary system infection and sexually transmitted diseases. Redundant prepuce or phimosis can cause urinary tract infections that may lead to chronic prostatitis, which presents as one or more symptoms such as back pain, impotence, prospermia, etc. Removing redundant prepuce or phimosis is a generally-accepted method of preventing these types of diseases.

Most circumcision devices in use today utilize a glans ferrule (interior ring) and used in conjunction with a fixture device (exterior ring). During the surgical process or the removal of the necrotic prepuce, movement of the glans during the procedure often causes patient pain and discomfort, and may further lead to hemorrhaging, which may affect healing time of the wound.

SUMMARY

The invention aims to provide a type of glans retainer used together with a circumcision apparatus. In order to realize the above-mentioned objective, the invention adopts the following technical solution: a glans retainer comprising an annular cover for covering the glans; fixing straps for fixing the annular cover to a circumcision apparatus that are connected to the periphery of the annular cover; wherein the annular cover is sized to match a glans.

The annular cover may comprise a circular or oval cross section.

Each fixing strap comprises an adhesive layer on its bottom.

In one embodiment, the annular cover and the fixing straps comprise medical adhesive tape.

In one embodiment, six fixing straps are provided.

The beneficial effects of the invention are as follows: with the annular cover covering the glans and the fixing straps connected with the circumcision apparatus, the glans is restricted from moving relative to the circumcision apparatus by virtue of tension in the fixing straps as they are secured to the annular cover. Therefore, in a surgery to remove the necrotic prepuce, pain is reduced and the probability of bleeding is lowered, making the surgical procedure more safe and reliable.

Further description of the invention is made below in combination with the attached figures and concrete implementation manners.

DETAILED DESCRIPTION OF THE PREFERRED EMBODIMENTS OF THE INVENTION

Figure 1:
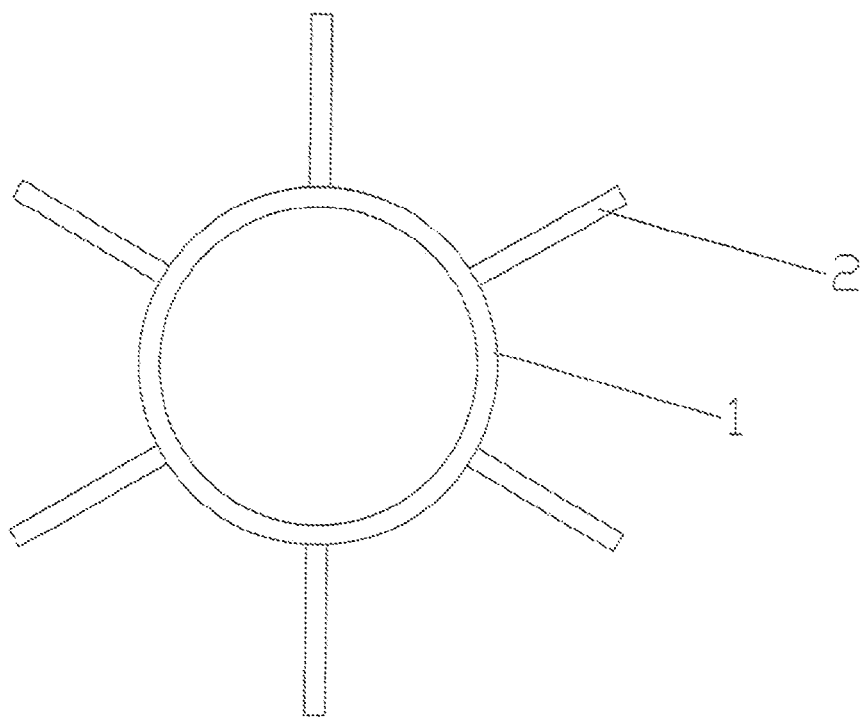
FIG. 1 illustrates the structure of glans retainer.
Figure 2:
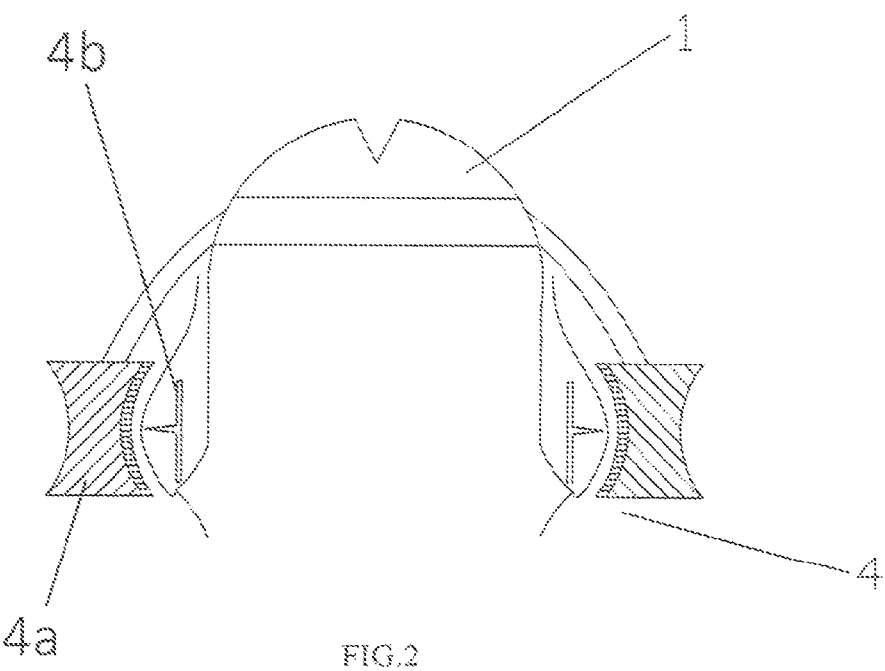
FIG. 2 illustrates a cross section of the glans retainer of FIG. 1.

FIGS. 1 and 2 illustrate one embodiment of a glans retainer, which may be used together with a circumcision apparatus so as to avoid pain and bleeding resulting from movement of the glans during removal of the necrotic prepuce during circumcising surgery.

The glans retainer comprises an annular cover 1 for covering the glans 3. Fixing straps 2 are connected on the periphery of the annular cover as shown for attaching the annular cover to an outer member 4a of circumcision apparatus 4. The annular cover is sized to match the glans 3, providing a snug fit of the annular cover over the glans.

The annular cover 1 may comprise a circular or oval cross section, so as to adapt to a glans or circumcision apparatus having different shapes. Each fixing strap 2 comprises an adhesive layer on its bottom for securing the annular cover to the circumcision apparatus 4. The annular cover 1 and the fixing straps 2 may comprise medical adhesive tape. The fixing straps may be arranged in 6 pieces, as shown in FIG. 1, or may be arranged freely in number and location.

FIG. 2 illustrates a cross sectional view of the annular cover 1 covering a glans and connected to the outer member 4a of circumcision apparatus 4 via the fixing straps 2. The circumcision apparatus comprises outer member 4a and inner member 4b. In this arrangement, the glans remains generally immobile relative to the circumcision apparatus from the tension of the fixing straps as they hold the annular cover against the glans. Therefore, during surgical removal of the necrotic prepuce, pain is reduced and the probability of bleeding is lowered, making the surgical procedure more safe and reliable.

I claim:

1. A glans retention system for use during circumcision surgery, comprising:
    a circumcision apparatus for removing a necrotic prepuce of a penis during the circumcision surgery, comprising an inner member and an outer member with a foreskin of the penis positionable therebetween;
    means for retaining a glans of the penis relative to the outer member during the circumcision surgery comprising an annular glans cover sized and shaped to match a shape of a glans of the penis; and
    means for securing the retaining means to the outer member during the circumcision surgery, wherein the means for securing the retaining means to the outer member comprises fixing straps connected under tension to the outer member and a periphery of the annular glans cover;
    wherein the means for retaining a glans is sized to match the glans, and is positioned around the glans and above the inner and outer members during the circumcision surgery.

2. The glans retention system of claim 1, wherein:
    the annular cover comprising a circular or oval cross section.

3. The glans retention system of claim 1, wherein:
    the straps comprise an adhesive layer.

4. The glans retention system of claim 1, wherein:
the means for retaining means a glans and the means for securing the means for retaining a glans each comprise medical adhesive tape.

5. The glans retention system of claim 1, wherein the annular glans cover comprises an annular ring that allows an entire tip of the penis to be exposed.

6. A glans retention system for use during circumcision surgery, comprising:
a circumcision apparatus for removing a necrotic prepuce of a penis during the circumcision surgery, the circumcision apparatus comprising:
an inner member; and
an outer member with a foreskin of the penis positionable therebetween; and
an annular glans cover, sized and shaped to match a shape of a glans of the penis, comprising a plurality of fixing straps connected on a periphery of the annular glans cover and attached to the outer member under tension, configured to restrain the glans relative to the outer member during the circumcision surgery, wherein the annular glans cover is positioned around the glans and above the inner and outer members during the circumcision surgery.

7. The glans retention system as claimed in claim 6, wherein:
the annular glans cover comprises a circular or oval cross section.

8. The glans retention system as claimed in claim 6, wherein:
each of the plurality of fixing straps comprises an adhesive layer on its bottom.

9. The glans retention system as claimed in claim 6, wherein:
the annular glans cover and the plurality of fixing straps comprise medical adhesive tape.

10. The glans retention system as claimed in claim 6, wherein:
the plurality of fixing straps comprise six straps.

11. The glans retention system of claim 6, wherein the annular glans cover comprises an annular ring that allows an entire tip of the penis to be exposed.

12. A method of restraining a glans during circumcision surgery, comprising:
providing the glans retention system of claim 6;
placing the circumcision apparatus over a penis to be circumcised;
placing the annular glans cover over the glans; and
securing the annular glans cover to the circumcision apparatus.

13. The method of claim 12, wherein the annular glans cover comprises an annular ring that allows a tip of the penis to be exposed.

* * * * *